United States Patent [19]

Zeikus et al.

[11] Patent Number: 4,814,267

[45] Date of Patent: Mar. 21, 1989

[54] METHOD FOR PREPARING HIGH CONVERSION SYRUPS AND OTHER SWEETENERS

[75] Inventors: Joseph G. Zeikus, Okemos; Badal C. Saha, East Lansing, both of Mich.

[73] Assignee: Michigan Biotechnology Institute, Lansing, Mich.

[21] Appl. No.: 946,813

[22] Filed: Dec. 29, 1986

Related U.S. Application Data

[63] Continuation-in-part of Ser. No. 652,585, Sep. 18, 1984, Pat. No. 4,647,538.

[51] Int. Cl.$^4$ .................. C12P 19/22; C12N 9/26; C12R 1/145
[52] U.S. Cl. .................................... 435/95; 435/201; 435/842
[58] Field of Search .................. 435/95, 162, 201

[56] References Cited

U.S. PATENT DOCUMENTS

| | | | |
|---|---|---|---|
| 3,922,196 | 11/1975 | Leach et al. | 195/31 R |
| 3,922,197 | 11/1975 | Leach et al. | 195/31 R |
| 3,922,198 | 11/1975 | Kuske et al. | 195/31 R |
| 3,922,199 | 11/1975 | Hebeda et al. | 195/31 R |
| 3,922,200 | 11/1975 | Walon et al. | 195/31 R |
| 3,992,261 | 11/1976 | Takasaki et al. | 195/31 R |
| 3,998,696 | 12/1976 | Yomoto et al. | 195/31 R |
| 4,113,509 | 9/1978 | Leach et al. | 127/29 |
| 4,199,372 | 4/1980 | Walon | 127/40 |
| 4,529,696 | 7/1985 | Takasaki et al. | 435/99 |
| 4,594,322 | 6/1986 | Thompson et al. | 435/95 |
| 4,628,031 | 12/1986 | Zeikus et al. | 435/205 |
| 4,647,538 | 3/1987 | Zeikus et al. | 435/95 X |

OTHER PUBLICATIONS

H. H. Hyun and J. G. Zeikus, May 1985. Simultaneous and Enhanced Production of Thermostable Amylases and Ethanol from Starch by Cocultures of Clostridium Thermosulfurogenes and Clostridium Thermohydrosulfuricum, Applied and Environmental Microbiology, vol. 49, No. 5, pp. 1174–1181.

H. H. Hyun and J. G. Zeikus, May 1985. General Biochemical Characterization of Thermostable Pullulanase and Glucoamylase from Clostridium Thermohydrosulfuricum, Applied and Environmental Microbiology, vol. 49, No. 5, pp. 1168–1173.

H. H. Hyun and J. G. Zeikus, May 1985. General Biochemical Characterization of Thermostable Extracellular $\beta$-Amylase from Clostridium Thermosulfurogenes, Applied and Environmental Microbiology, vol. 49, No. 5, pp. 1162–1167.

H. H. Hyun and J. G. Zeikus, Dec. 1985. Regulation and Genetic Enhancement of Glucoamylase and Pullulanase Production in Clostridium Thermohydrosulfuricum, Journal of Bacteriology, vol. 164, No. 3, pp. 1146–1152.

H. H. Hyun and J. G. Zeikus, Dec. 1985. Regulation and Genetic Enhancement of $\beta$-Amylase Production in Clostridium Thermosulfurogenes, Journal of Bacteriology, vol. 164, No. 3, pp. 1162–1170.

*Primary Examiner*—Blondel Hazel
*Assistant Examiner*—Charles L. Patterson, Jr.
*Attorney, Agent, or Firm*—Quarles & Brady

[57] ABSTRACT

An improved method of preparing high maltose conversion syrups and other sweeteners from starch substrates comprises saccharifying the starch at higher temperatures than presently used with environmentally compatible thermostable $\beta$-amylase and other thermostable enzymes.

6 Claims, 1 Drawing Sheet

METHOD FOR PREPARING HIGH CONVERSION SYRUPS AND OTHER SWEETENERS

RELATED APPLICATION

This application is a continuation-in-part of the earlier U.S. application Ser. No. 652,585, filed Sept. 18, 1984, now U.S. Pat. No. 4,647,538.

FIELD OF THE INVENTION

The present invention relates generally to the preparation of syrups and sweeteners. More particularly, it relates to the enzymatic conversion of all starch substrates to high maltose conversion syrups and other sweeteners.

BACKGROUND OF THE INVENTION

Syrups and other sweeteners are used in the brewing, baking, soft drinks, canning and confectionery industries. Some of the more valuable syrups contain maltose; they are of industrial importance primarily because of their functional characteristics rather than their sweetness. Among the important functional characteristics of high maltose syrups are low hygroscopicity, low viscosity in solution, resistance to crystallization, low sweetness, reduced browning capacity, and good heat stability. Thus, maltose containing syrups can be used as moisture conditioners, crystallization inhibitors, stabilizers, carriers and bulking agents.

There are three important types of maltose containing syrups: (1) high maltose syrups; (2) extremely high maltose syrups; and, (3) high conversion syrups. The high maltose syrups have DE's (dextrose equivalents) of about 35–50, and a maltose content of 45–60%; the extreme high maltose syrups have a DE of about 45–60 and a maltose content of about 70–85%; and the high conversion syrups normally have a glucose content of 35–43%, a maltose content of about 30–47%. All of the foregoing syrups also contain some maltotriose.

The high conversion syrups are especially important because they have a high DE (e.g. 60–70) but they are stable enough to resist crystallization even at low temperatures down to 4° C. and concentrations of up to 80–83% dry substance. Because of their high content of fermentable sugars (about 80% consisting mainly of maltose and glucose) these syrups are widely used in the brewing of beer, bread making and in the fermentation industries.

Highly purified maltose is also valuable and may be preferred to glucose in intravenous feeding at high concentrations because of its lower osmotic pressure and its slower release of glucose. As a result it also is more suitable for use in food for diabetics.

As the demand for starch derived syrups and sweeteners grows, it can be expected that the various maltose-containing syrups will assume stronger places as industrial commodities for use primarily as food ingredients. However, the commercial utilization of high maltose syrups is still limited at the present time due to the high cost of the enzymes used to prepare such syrups.

The production of the various maltose syrups from starch substrates generally involves a two step process. The first is the liquefaction of starch. In this step, the starch usually is suspended or dispersed in an aqueous medium and gelatinized by heat and then partially hydrolyzed using a thermostable alpha-amylase. The dry substance concentration of the starch suspensions or dispersions used in industry are usually about 30–40% and as a result the viscosity is extremely high after gelatinization. The temperatures necessary for jet cooking to obtain total gelatinization are usually about 105°–110° C. for most starch substrates. The preferred reaction conditions are usually a pH of about 6.0–6.5, a calcium ion concentration of 20–80 ppm, and a temperature of 90°–100° C. The hydrolytic reaction is terminated when the DE is about 5–10. Liquefaction also can be carried out by acidifying a starch slurry to a pH of 1.5–2.0 followed by heating at 140°–150° C. for 5–10 minutes.

The second step in the preparation of syrups from starch substrates is saccharification. Saccharification is the hydrolysis of oligosaccharides or dextrins to low molecular weight sugars such as glucose, maltose or mixture of these or their by-products. This is commercially done by a maltose producing enzyme such as a plant or microbial beta-amylase or fungal alpha-amylase. The saccharification is usually carried out at a pH of about 5.0–5.5 and at lower temperatures of about 50°–55° C. The lower temperatures are required because the commercially available saccharifying enzymes are heat labile. Furthermore, the action beta-amylases or fungal alpha-amylases is limited; they cannot act on alpha (1–6) linkages. Therefore, in order to produce extremely high maltose syrups it is necessary to also employ debranching enzymes such as isoamylase or pullulanase, which act on the alpha linkages, in addition to the beta-amylase or the fungal alpha-amylase. The high conversion syrups also are produced by saccharifying a liquefied starch at the lower temperatures and using both a beta-amylase or a fungal alpha-amylase and a glucoamylase. The use of the lower temperatures during saccharification present handling problems because of the higher viscosities and yield problems because of the formation of retrograde products.

There is a need for a method employing saccharifying enzymes at higher temperatures than those normally employed so that the problems associated with the low temperatures can be avoided.

BRIEF SUMMARY OF THE INVENTION

It is an object of the present invention to provide an improved method for preparing maltose containing syrups from starch substrates by using higher temperatures than used in the past with environmentally compatible thermostable enzymes.

A further object is to provide a method of preparing high conversion syrups from starch substrates at temperatures above 70° C. using environmentally compatible saccharifying enzymes, such as beta-amylases, glucoamylases and pullulanases.

It is a still further object to provide a method of preparing maltose syrups directly from starch without first jet cooking the starch by using a thermostable beta-amylase in combination with other thermostable enzymes.

The method of the present invention generally comprises treating starch or a starch substrate such as liquid starch with a thermostable beta-amylase and optionally other thermostable enzymes at a temperature from about 70° C. to about 80° C. until the starch or starch substrate has been substantially all converted to a syrup containing maltose, glucose and maltotriose.

The thermostable beta-amylase which is preferred for use in the present invention is a highly thermostable enzyme prepared from *Clostridium thermosulfurogenes* in the manner described in U.S. patent application Ser. No. 652,585 filed Sept. 18, 1984, which is incorporated by reference herein. The thermostable beta-amylase also is described in the publication of H. H. Hyun and J. G. Zeikus, in *Applied and Environmental Microbiology* Volume 49, pp. 1162-1173 (1985).

A particularly suitable thermostable glucoamylase and a pullulanase for use in some embodiments of the method of present invention are those obtained from *Clostridium thermohydrosulfuricum* as described in U.S. Pat. No. 4,628,031, which is incorporated by reference herein. Of course, commercially available enzymes can also be used with the thermostable beta-amylase.

A particular useful alpha-amylase for use in the method of the present invention with the thermostable beta-amylase is the commercially available alpha-amylase obtained from *Bacillus licheniformis*.

DESCRIPTION OF THE PREFERRED EMBODIMENT

Figure 1:
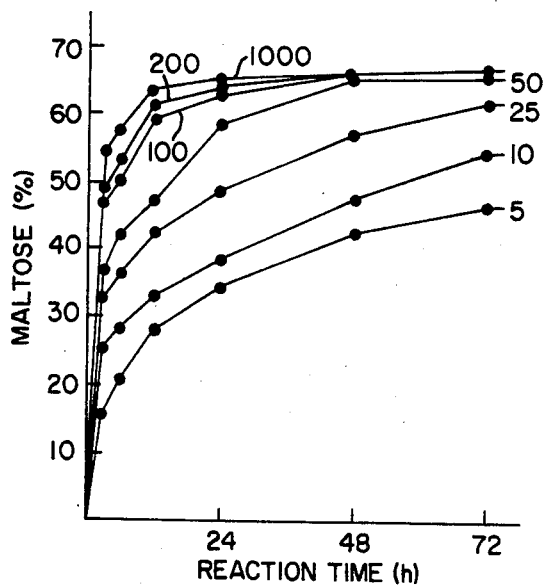
FIG. 1. shows the effect on maltose production from a maltodextrin DE 10 suspension (35% w/w) at 75° C. using 5, 10, 25, 50, 100, 200 and 1000 units of β-amylase per gram of substrate.

In the preferred embodiment of the method of the invention a high conversion syrup is prepared from an aqueous suspension of maltodextrin DE 10 (35% w/w) using a pH of 6.0 and a temperature of about 75° C. The β-amylase used is that derived from *C. thermosulfurogenes* and the glucoamylase is that derived from *C. thermohydrosulfurium*. A typical syrup composition prepared by this method will contain about 37% glucose, 39% maltose, 6-7% of maltotriose and have a DE of about 62.

When an extremely high maltose syrup is to be prepared, a debranching enzyme, such as the pullulanase from *C. thermohydrosulfurium* is used with the prepared β-amylase. The process is conducted at a pH of about 6.0 at about 75° C. until the reaction is substantially complete. The syrup produced has a DE of about 45-60 and a maltose context of about 70-85%.

When the syrup to be prepared from starch is to be a high maltose syrup, the β-amylase may be used or with a thermostable alpha-amylase. The syrup obtained contains about 50-62% maltose, 18-25% maltotriose and 5-14% glucose. The DE of the syrup is usually 45-52.

If it is desired to have a syrup which has both a high maltose and high maltotriose content, it can be prepared directly from corn starch by simply using a commercial alpha-amylase, the preferred thermostable β-amylase and a pullulanase (Promozyme) in a two-stage process in which the starch is first treated with the alpha-amylase and beta-amylase at about 75° and then the pullulanase is added at 60° C. A typical syrup obtained may have a maltose concentration of about 55-60%, a maltotriose concentration of about 28-31% and a glucose concentration of about 5-7%. The DE of the syrup will be about 45-48.

The practice of the present invention will be further illustrated by the examples which are described hereinafter.

The β-amylase employed in the Examples is that obtained from *Clostridium thermosulfurogenes* (ATCC 33743) which is on deposit with the American Type Culture Collection in Rockville, Md. The enzyme may be prepared as described in the aforementioned U.S. patent application Ser. No. 652,585.

The glucoamylase which is employed in the Examples is that derived from *Clostridium thermohydrosulfuricum* (ATCC 33223) as described in U.S. Pat. No. 4,628,031.

The alpha-amylase which is employed is that obtained from *Bacillus licheniformis* and which is commercially available as the product Thermamyl 120L.

The pullulanase which is used at the lower temperatures is that available from Novo Laboratories, Inc. U.S.A. under the name Promozyme.

The pullulanase used at the higher temperatures (above 65° C.) is that derived from *Clostridium thermohydrosulfurium* (ATCC 33223) as described in U.S. Pat. No. 4,628,031.

The various starch substrates used in the examples were maltodextrin DE 10 which was supplied by A. E. Staley Company U.S.A. and granular starch which was purchased from Sigma Chemical Company U.S.A.

The β-amylase activity was assayed using a reaction mixture (5 ml) consisting of boiled soluble starch solution (2%), acetate buffer (50 mM, pH 6.0) and appropriately dilluted enzyme solution. After incubation for 30 minutes at 60° C. the reducing sugar liberated was measured by the dinitrosalicylic acid method. One unit of β-amylase was defined as the amount of enzyme which liberated one micro mole of reducing sugar as a glucose standard per minute under the above conditions.

Pullulanase activity was assayed using a reaction mixture (1 ml) that contained pullulan (1%), acetate buffer (50 mM, pH 6.0) and enzyme solution. After a 30 minute reaction at 60° C., the amount of reducing sugar formed was determined by the dinitrosalicylic acid method. One unit of pullulanase activity was defined as that amount of enzyme that produces 1 micro mole of reducing sugar with glucose as standard per minute under the conditions described.

Glucoamylase activity was assayed using a reaction mixture (1 ml) consisting of boiled soluble starch (2%) in acetate buffer (50 mM, pH 6.0) and the enzyme solution. After incubation at 60° C. for 30 minutes, the reaction mixture was kept in a steam bath for 10 minutes and centrifuged to remove insoluble materials. The released glucose was estimated by the hexokinase and glucose-6-phosphate dehydrogenase method [H. Bergmeyer (ed.) 1965. Methods of enzymatic analysis. Academic Press, Inc., New York]. One unit of glucoamylase is defined as the amount of enzyme that produced 1 umole of glucose per minute under the assay conditions described above.

Alpha-amylase activity was assayed by determining the achromatic point of starch-iodine complexes. The reaction mixture (5 ml) containing boiled soluble starch (2%) and acetate buffer (50 mM, pH 6.0), $CaCl_2$ (5 mM) and enzyme solution was incubated at 60° C. At suitable time intervals, 0.2 ml of the reaction mixture was used for the observation of the color change by adding 0.2 ml of 0.01N iodine solution and hence for the determination of the time elapsed before the achromatic stage was reached. The standard color for the achromatic point was made by mixing the iodine solution and the reaction mixture without soluble starch. One unit of alpha-amlyase activity is that amount of enzyme which is able to convert the color of the reaction mixture containing boiled soluble starch with iodine to the achromatic point in 10 min under the above conditions.

Fermentability was estimated as the sum of $DP_1$, $DP_2$ and $DP_3$ saccharides ($DP_1$=monosaccharide assumed to be predominantly glucose; $DP_2$=disaccharide assumed to be predominantly maltose; and $DP_3$=trisaccharide assumed to be predominantly maltotriose) on the assumption that these simple sugars are completely utilized by brewing yeast and the fermentability as determined by laboratory fermentation test is in good agreement with calculated values for a variety of starch hydrolysis products (Hebeda, R. E. and Styrlund, C. R. Cereal Foods World 31, 685–687 (1986)).

Qualitative and quantitiative analysis of starch hydrolysis products were performed by high pressure liquid chromatography. The separation system consist of a multisolvent delivery system (600, Waters Chromatography Division, Millipore Corporation, Milford, MA) equipped with a autosampler (712 WISP, Waters), a refractive index detector (410 Differential refractometer, Waters), Data module (740, Waters) and an oligosaccharide analysis column (300×7.8 mm, Aminex HPX-42A; Bio-Rad Laboratories, Richmond, CA) fitted with carbohydrate deashing system (Bio-Rad). Starch hydrolyzates were centrifuged before loading onto the column.

The residual starch was washed with water, dried overnight in an oven at 50° C. and analyzed for moisture. DE was measured according to standard analytical methods (E-26) of the Corn Industries Research Foundation.

The process of the present invention will be illustrated in detail by way of example.

Example 1

An amount of maltodextrin DE 10 was dissolved in water to give a final solid concentration of 10 to 50% by weight. The pH was adjusted to 5.0 and the preferred β-amylase (50 to 1,000 units/g substrate) was added at 75° C. The reaction was complete in 48–72 hr. The final hydrolyzates contained about 60–65% maltose, about 6–9% maltotriose and less than 1% glucose and higher saccharides especially limit dextrins 25–30%, DE 35–40. The concentration of fermentables was 67–71%.

Table 1 and FIG. 1 shows the effect of different substrate and enzyme concentrations on maltose production using the preferred β-amylase in the manner described in Example 1.

TABLE 1

Effect of substrate (maltodextrin DE 10) concentration on maltose production by MBI beta-amylase

| Substrate[a] | | Maltose (%)[b] | | | | |
|---|---|---|---|---|---|---|
| (%) (w/v) | (w/w) | 6 h | 12 h | 24 h | 48 h | 72 h |
| 10 | 10 | 55.72 | 62.19 | 64.26 | 64.48 | 65.17 |
| 20 | 20 | 56.73 | 59.86 | 62.91 | 64.08 | 65.36 |
| 30 | 27 | 53.76 | 59.00 | 61.83 | 63.97 | 65.10 |
| 35 | 31 | 53.30 | 59.84 | 62.06 | 64.18 | 64.62 |
| 40 | 35 | 53.33 | 59.41 | 61.09 | 64.23 | 65.54 |
| 50 | 43 | 38.04 | 43.07 | 49.00 | 52.54 | 54.50 |

[a]Reaction at pH 5.0 and 75° C.; enzyme used, 200 units/g substrate.
[b]Determined by HPLC analysis.

Example 2

To produce extremely high maltose syrups, a (pullulanase) (Promozyme) was used with the prepared β-amylase. Maltrodextrin DE 10 was dissolved in water to give a final solid concentration of 35% by weight. The pH was adjusted to 5.0. The β-amylase was used at a concentration of 200 units/g substrate and pullulanase at 50 units/g substrate unless otherwise specified. The following six different conditions were employed.

(1) The β-amylase was allowed to act at 75° C. for 24 hr and then pullulanase was added after adjusting the temperature at 60° C. The reaction was complete in 72 hr.

(2) The β-amylase and pullulanase were added to the maltodextrin solution at 60° C. The reaction was continued at 60° C. for 24 hr and then the temperature was raised to 75° C. The reaction was allowed to continue up to 72 hr.

(3) The pullulanase was first allowed to act at 60° C. for 24 hr and then the β-amylase was added and the temperature was increased to 75° C.

(4) The β-amylase and pullulanase were added together at 60° C.

(5) The β-amylase was first allowed to work at 60° C. for 24 hr and then the pullulanase was added at the same temperature.

(6) The pullulanase was first added at 60° C. and allowed to act for 24 hr after which the β-amylase was added at the same temperature.

A practical period for saccharification was within 72 hr in total and the final hydrolyzate contained about 75–85% maltose, 10–15% maltotriose, 1–3% glucose according to HPLC analysis. The DE was about 47–52, the fermentables were 88–97%.

Figure 2:
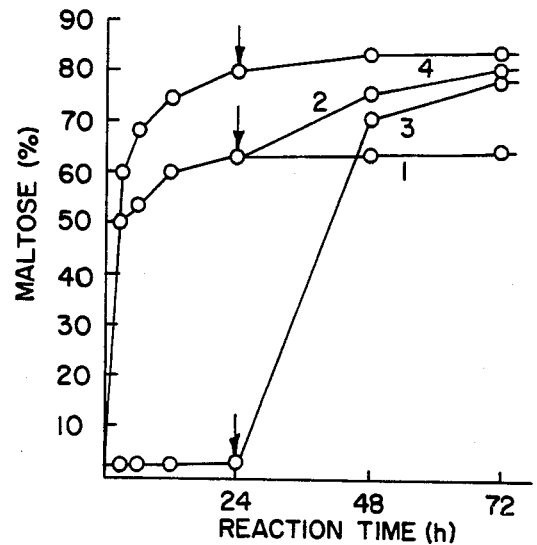
FIG. 2 shows the effect of the addition of other enzymes and temperature changes on the time course of maltose production from a maltodextrin DE 10 solution (35% w/w) at varying temperatures using β-amylase and pullulanase. Line No. 1 represents β-amylase at 75°; line No. 2 beta-amylase at 75° C. for 24 hours and then beta-amylase and pullulanase (Promozyme, Novo Ind.) at 60° C.; line No. 3 pullulanase (Promozyme) at 60° C. for 24 hours and then beta-amylase at 75° C.; and, line No. 4 beta-amylase and pullulanase (Promozyme) at 60° C. for 24 hours and then raising the temperature to 75° C. The arrows indicate the time of addition of second enzyme and/or change of temperature.
Figure 3:
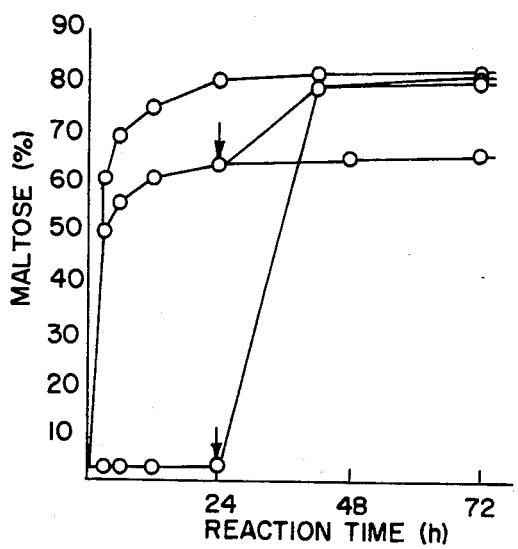
FIG. 3 shows the time course of maltose production from a solution of maltodextrin DE 10 (35% w/w) at 60° C. using beta-amylase (200 units/gram of substrate) and pullulanase (Promozyme) (50 units/gram of substrate). Line No. 1 represents β-amylase alone; line No. 2 β-amylase along for 24 hours and then the combination of beta-amylase and pullulanase; line No. 3 pullulanase alone for 24 hours and then the addition of β-amylase and line No. 4 the use of the combination of β-amylase and pullulanase from the start; and, FIG. 4 shows the effect of the combined use of alpha amylase (6 units per gram of substrate) and β-amylase (200 units per gram of substrate) on maltose production from a corn starch suspension (28% w/w) at 75° C.

FIG. 2 shows the effect on the time course of maltose production from maltodextrin by using both β-amylase and pullulanase under the conditions of Example 2 (1), (2) and (3) as compared to a β-amylase control. FIG. 3 shows the effect on the time course of maltose production using the conditions of Example 2 (4), (5) and (6).

Example 3

High conversion syrups were prepared from maltodextrin DE 10 by using the preferred β-amylase and the preferred glucoamylase from C. thermohydrosulfurium. The maltodextrin DE 10 was dissolved in water (35% w/w) and the pH was adjusted to pH 6.0. Then the β-amylase (200 units/g substrate) and the glucoamylase (2 units/g substrate) were added. The final substrate concentration was 35% (w/w). The whole reaction mixture was incubated at 75° C. The syrup contained glucose about 37%, maltose about 39% and maltotriose about 6-7%, DE 62, the fermentables were about 85%.

Example 4

A high maltose syrup was prepared from granular starch without first jet cooking the starch using alpha-amylase (Thermamyl 120L) and the preferred β-amylase. The starch was slurried in water to give a final solid content of about 28-35% (w/w). Calcium was added if necessary to give a concentration of about 50 ppm. The pH was adjusted to 6.0 and alpha-amylase (3-30 units/g substrate) and β-amylase (200 units/g substrate) were added. The starch suspension was agitated slowly at 75° C. After 72 hr, the digest was analyzed for DE, sugar composition and residual starch. The syrup in 72 h contained about 50-62% maltose, 18-25% maltotriose and 5-14% glucose, DE 45-52, fermentables 80-94%, and residual starch available for recycling was 3-10%.

Figure 4:
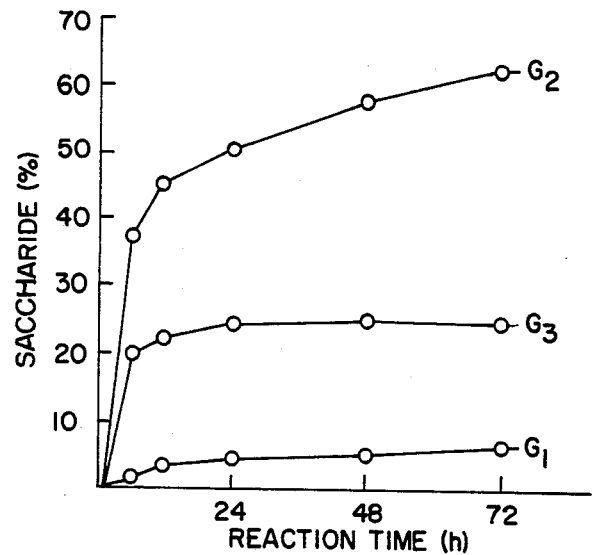

The time course of maltose production from corn starch using the combination of alpha-amylase and β-amylase is shown in FIG. 4 and the compositions of syrups obtained using different concentrations of alpha-amylase and different starches are shown in Tables 2 and 3, respectively.

TABLE 2

Effect of alpha-amylase concentration on maltose syrups production by beta-amylase from corn starch

| Enzyme (units/g substrate) | Saccharide (%) | | |
|---|---|---|---|
| | Glucose | Maltose | Maltotriose |
| alpha$_3$ beta$_{200}$ | 3.75 | 53.48 | 22.84 |
| alpha$_6$ beta$_{200}$ | 6.50 | 61.98 | 24.30 |
| alpha$_{12}$ beta$_{200}$ | 9.12 | 60.73 | 22.68 |
| alpha$_{30}$ beta$_{200}$ | 13.23 | 59.56 | 18.30 | substrate used, 28% (w/w)
Reaction time, 72 h at 75° C.
alpha, alpha-amylase
beta, beta-amylase

TABLE 3

Maltose syrups production from various starches

| Starch | Saccharide (%) | | |
|---|---|---|---|
| | Glucose | Maltose | Maltotriose |
| Corn | 6.50 | 61.98 | 24.30 |
| Wheat | 6.36 | 59.44 | 27.49 |
| Potato | 6.13 | 57.10 | 21.41 |
| Soluble | 6.30 | 62.76 | 24.74 |

Substrate used, 28% (w/w)
Reaction time, 72 h at 75° C.

Example 5

A high maltose conversion syrup having a higher maltotriose content and less glucose content than that obtained in Example 4 from granular corn starch was obtained using alpha-amylase, β-amylase and pullulanase (Promozyme) in a two stage process with respect to temperature of the starch conversion mixture. Corn starch was suspended in water such that it had a solid content of 28% by weight. Calcium was added in the form of CaCl$_2$ to give a concentration of about 50 ppm. The pH was adjusted to 6.0. First the alpha-amylase (6 units/g substrate) and the β-amylase (200 units/g substrate) were added. The starch suspension was then agitated slowly at 75° C. for 24 hr. Next, the pullulanase (10 to 100 units/g substrate) was added at 60° C. and the reaction was continued for another 48-72 hr. The typical syrup composition was 55-60% maltose, 28-31% maltotriose and 5-7% glucose, DE 45-48, fermentables were 88-96% and residual starch available for recycling 4-7%. The addition of pullulanase did not increase the maltose content of the hydrolyzate. This type of syrup is called maltose-maltotriose syrup. (H. W. Leech, R. E. Hebeda and D. J. Holik, U.S. Pat. No. 4,113,509; Sept. 12, 1978).

The compositions of syrups resulting from a series of experiments using different concentrations of pullulanase (Promozyme) are shown in Table 4.

TABLE 4

Maltose maltotriose syrups production from corn starch

| Enzyme (units/g substrate) | Saccharide (%) | | |
|---|---|---|---|
| | Glucose | Maltose | Maltotriose |
| alpha$_6$ beta$_{200}$ P$_{10}$ | 5.10 | 59.91 | 30.36 |
| alpha$_6$ beta$_{200}$ P$_{20}$ | 5.34 | 60.07 | 30.85 |
| alpha$_6$ beta$_{200}$ P$_{50}$ | 6.87 | 59.28 | 30.21 |
| alpha$_6$ beta$_{200}$ P$_{100}$ | 6.33 | 59.22 | 29.97 |

Substrate used, 28% (w/w)
Reaction time, 72 h (75° C., 60° C.)
alpha, alpha-amylase; beta, beta-amylase; P, pullulanase

Example 6

A granular ungelatinized starch suspension (28-35% w/w) was mixed with alpha-amylase (6 u/g), the preferred β-amylase (200 u/g) and pullulanse (Promozyme) (50 u/g) at a temperature of about 60° C. and a pH of about 6.0. The final starch concentration was 25% by weight. After 120 hours the syrup composition is about 45% maltose, about 28% maltotriose, and about 6% glucose, the DE is about 40.

Example 7

The procedure of Example 6 may be repeated with substantially the same results using an equivalent amount of the pullulanase from C thermohydrosulfuricum. However the reaction time may be reduced by running the reaction at 75° C.

It will be appreciated by those skilled in the art that a number of changes and modifications may be made without departing from the spirit and scope of the invention. For example, other thermostable enzymes may be used in place of the alpha amylase, glucoamylase and pullulanase described.

We claim:

1. In a method of preparing a high maltose conversion syrup from a starch substrate, the improvement which comprises enzymatically treating the starch substrate with a thermostable β-amylase from *Clostridium thermosulfurogenes* at a pH of about 5.0 to about 6.0 and a temperature of above about 70° C. to substantially convert the starch substrate to a syrup containing maltose.

2. A method of claim 1 in which the substrate is an aqueous suspension of starch which has not been previously jet cooked, the pH is about 6.0, α-amylase is present, and the suspension is held at about 75° C. until a syrup is obtained containing at least 50% maltose.

3. A method of claim 1 in which the substrate is maltodextrin, the pH is about 5.0 and the syrup contains maltose, maltotriose and less than 1% glucose.

4. A method of claim 1 in which the substrate is also treated with a pullulanase.

5. A method of claim 1 in which the substrate is a maltodextrin aqueous suspension, the pH is about 6.0, a glucoamylase is present and the syrup contains glucose, maltose and maltotriose.

6. A method of claim 1 in which the substrate is an aqueous suspension of starch and an α-amylase and a pullulanase are present.

* * * * *